(12) United States Patent
Lee et al.

(10) Patent No.: US 7,601,392 B2
(45) Date of Patent: Oct. 13, 2009

(54) ORGANIC-METAL PRECURSOR MATERIAL AND METHOD OF MANUFACTURING METAL THIN FILM USING THE SAME

(75) Inventors: Jung-hyun Lee, Yongin-si (KR); Bum-seok Seo, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 506 days.

(21) Appl. No.: 11/513,999

(22) Filed: Aug. 31, 2006

(65) Prior Publication Data

US 2007/0071892 A1 Mar. 29, 2007

(30) Foreign Application Priority Data

Sep. 23, 2005 (KR) .................... 10-2005-0088714

(51) Int. Cl.
*C07F 15/00* (2006.01)

(52) U.S. Cl. .................... 427/248.1; 427/569; 556/136; 556/137

(58) Field of Classification Search ............. None
See application file for complete search history.

(56) References Cited

U.S. PATENT DOCUMENTS

2002/0074582 A1* 6/2002 Hiratani et al. ............. 257/296
2005/0085031 A1* 4/2005 Lopatin et al. ............. 438/222

* cited by examiner

*Primary Examiner*—Timothy H Meeks
*Assistant Examiner*—Joseph Miller, Jr.
(74) *Attorney, Agent, or Firm*—Cantor Colburn LLP

(57) ABSTRACT

Provided are an organic-metal precursor material that can be readily decomposed without reacting with an oxidant, a method of manufacturing a metal thin film using the organic-metal precursor material, and a metal thin film prepared using the organic-metal precursor material. The organic-metal precursor material is an organic molecule having lone-pair electrons selected from the group consisting of ether, amine, tetrahydrofuran (THF), a phosphine group, and a phosphite group, and has a structure of covalent coordination bond.

12 Claims, 4 Drawing Sheets

As-dep.

(A)

500°C 10min (B)

600°C 10min (C)

ORGANIC-METAL PRECURSOR MATERIAL AND METHOD OF MANUFACTURING METAL THIN FILM USING THE SAME

CROSS-REFERENCE TO RELATED PATENT APPLICATION

This application claims priority to Korean Patent Application No. 10-2005-0088714, filed on Sep. 23, 2005, and all the benefits accruing therefrom under 35 U.S.C. §119, and the contents of which are incorporated herein by reference in their entirety.

BACKGROUND OF THE INVENTION

1. Field of the Invention

The present invention relates to a new organic-metal precursor material and a method of manufacturing a metal thin film for a capacitor electrode using the same, and more particularly, to a new organic-metal precursor material that can be readily decomposed without reacting with an oxidant, and a method of manufacturing a metal thin film using the same.

2. Description of the Related Art

Conventionally, ruthenium ("Ru") has received attention as an electrode material for a DRAM capacitor, or as a diffusion barrier film material for blocking the diffusion of a wire material such as copper ("Cu") in a semiconductor device. However, to deposit ruthenium, a ruthenium precursor is decomposed using an oxidant such as oxygen. As a result, oxygen is often trapped with the ruthenium during deposition under these conditions, and can oxidize the ruthenium and increase the specific resistance of the electrode material or of a wire material adjacent to the ruthenium. This has delayed the application of conventional ruthenium electrodes.

BRIEF SUMMARY OF THE INVENTION

In an embodiment, the present invention provides a new organic-metal precursor material that can be decomposed without reacting with an oxidant, and a method of manufacturing a metal thin film using the organic-metal precursor material.

According to an embodiment of the present invention, there is provided an organic-metal precursor material having the following chemical formula:

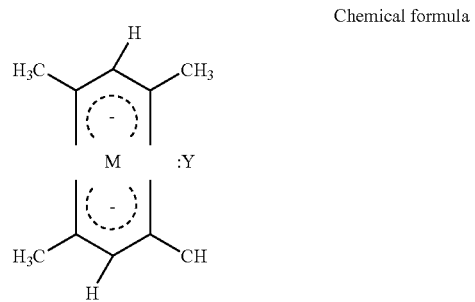

Chemical formula wherein M is ruthenium or iridium ("Ir"), and Y is an organic molecule having lone-pair electrons.

The organic molecule having lone-pair electrons may be an organic molecule that comprises oxygen ("O"), nitrogen ("N"), or phosphorus ("P"), and may be a material selected from the group consisting of an ether, an amine, tetrahydrofuran ("THF"), a phosphine, and a phosphite.

According to another embodiment of the present invention, there is provided a method of manufacturing an organic-metal precursor material comprising: preparing the organic-metal precursor material having the above chemical formula; forming a source gas by evaporating the organic-metal precursor material; and depositing a metal thin film on a substrate in a vacuum chamber using chemical vapor deposition ("CVD") by supplying the source gas into a vacuum chamber. In a specific embodiment, CVD may comprise atomic layer deposition ("ALD").

The preparing of the organic-metal precursor material can comprise: making a first solution by dissolving bis(2,4-dimethylpentadienyl)ruthenium (i.e., Ru(DMPD)$_2$) or bis(2,4-dimethylpentadienyl)iridium (i.e., Ir(DMPD)$_2$) in pentane; making a second solution by adding an organic molecule having lone-pair electrons selected from the group consisting of an ether, an amine, tetrahydrofuran (THF), a phosphine group, and a phosphite group in the first solution; stirring the second solution at room temperature to promote a covalent coordination reaction; and obtaining the organic-metal precursor material by vacuum distilling pentane from the second solution in which the covalent coordination reaction took place.

The organic-metal precursor material may be evaporated at a temperature of 150 to 250° C., and the metal thin film may be deposited at a temperature of 250 to 500° C.

The metal thin film may be deposited under a reductive reaction gas atmosphere by further supplying a reductive reaction gas that comprises H$_2$ or NH$_3$ gas into the vacuum chamber. Here, the H$_2$ gas may be supplied at a flow rate of 1 to 200 sccm, and the NH$_3$ gas may be supplied at a flow rate of 50 to 200 sccm. Specifically, the metal thin film may be deposited under a reductive reaction gas plasma atmosphere by generating a reductive reaction gas plasma in the vacuum chamber.

In an embodiment of the present invention, an organic-metal precursor material that can be readily decomposed without reacting with an oxidant is obtained, and a metal thin film that does not include oxygen can be manufactured. A metal thin film is thus obtained from the decomposition of the organic-metal precursor material. A metal thin film is also obtained as the reaction product of the organic-metal precursor compound and a reducing reaction gas. The metal thin film can be provided by a thermal reaction, with or without use of a plasma.

BRIEF DESCRIPTION OF THE DRAWINGS

The above and other features and advantages of the exemplary embodiments of the present invention will become more apparent by describing in detail exemplary embodiments thereof with reference to the attached drawings in which.

DETAILED DESCRIPTION OF THE INVENTION

An organic-metal precursor material and a method of manufacturing a metal thin film using the organic-metal precursor material will now be described more fully with reference to the accompanying drawings, in which exemplary embodiments of the invention are shown.

It will be understood that when an element is referred to as being "on" another element, it can be directly on the other element or intervening elements may be present therebetween. In contrast, when an element is referred to as being "deposited on" another element, the elements are understood to be in at least partial contact with each other, unless otherwise specified.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 1:
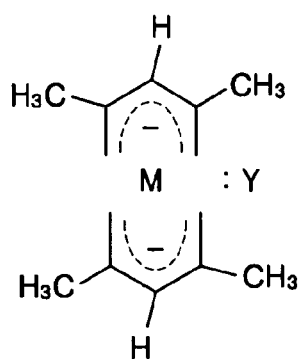
FIG. 1 is the chemical formula of an organic-metal precursor material according to an exemplary embodiment.

FIG. 1 is the chemical formula of an organic-metal precursor material according to an embodiment of the present invention. Here, M is ruthenium ("Ru") or iridium ("Ir"), and Y is an organic molecule having lone-pair electrons.

Referring to FIG. 1, an organic-metal precursor material has a structure in which an organic molecule having lone-pair electrons is covalently and coordinatively bonded to an organometallic compound having a C=C—M—C=C structure such as $Ru(DMPD)_2$ (where M is Ru). The organic molecule having lone-pair electrons is an organic molecule that includes oxygen O, nitrogen N, or phosphorus P, and can be a material selected from the group consisting of ether, amine, tetrahydrofuran (THF), phosphine, and phosphite. The organic-metal precursor material shown in the chemical formula in FIG. 1 can be readily decomposed without a chemical reaction with an oxidant such as oxygen. In an embodiment, the organic-metal precursor material is decomposed thermally. Therefore, it can be a useful source material for manufacturing thin (i.e., 1 to 100 nanometers, nm) metallic films, also referred to herein as "metal thin films" using chemical vapor deposition (CVD) or atomic layer deposition (ALD).

Specifically, the metal thin film manufactured using the organic metal precursor material and method as disclosed herein does not require decomposition of the precursor in oxygen atmosphere, and therefore the metal thin film so prepared does not include oxygen. In particular, the metal thin film prepared without oxygen does not include adsorbed oxygen, or oxygen present as an oxide of a metal of the thin film, such as, for example, ruthenium oxide. The presence of such oxides in a metal thin film, e.g., in an electrode material or diffusion barrier, can undesirably increase the electrical resistance of the metal thin film. In addition, the presence of oxygen in the metal thin film, such as trapped or adsorbed oxygen, or as metal oxide, can also undesirably act as a source of oxygen which can cause formation of undesirable electrically resistive oxides in adjacent metallic features such as wires, interconnects, capacitor plates, and the like. Accordingly, when a metal thin film, prepared using the organic metal precursor material and using a deposition method that is free of oxygen, is in turn used to form an electrode material or a diffusion barrier film for blocking the diffusion of a wire material such as copper in a semiconductor device, the specific resistance due to oxidation of the electrode material and/or the wire material is reduced. As used herein, "free of oxygen" means having oxygen present in an amount of less than 1,000 ppm, specifically less than 500 ppm, and still more specifically less than 100 ppm, expressed in volume parts per million units volume. In an embodiment, the metal thin film prepared from from the organic-metal precursor material is free of oxygen. In addition, the metal thin film manufactured in this way has a superior surface morphology with lower defectivity, higher uniformity, and a smoother topography, when compared to the surface morphology of a conventional metal thin film that is prepared using an oxygen decomposition process, and that contains oxygen. In an embodiment, the metal thin film comprises the decomposition product of the organic-metal precursor material.

The organic-metal precursor material expressed by the chemical formula in FIG. 1 can be obtained by the following method. A first solution is prepared by dissolving a ruthenium or iridium complex of DMPD, i.e., $Ru(DMPD)_2$ or $Ir(DMPD)_2$, in pentane. A second solution is obtained by adding an organic molecule having lone-pair electrons selected from the group consisting of ether, amine, THF, a phosphine group, and a phosphite group. The second solution is stirred at room temperature to promote a covalent coordination reaction. The organic-metal precursor material can then be obtained by performing vacuum distillation to remove pentane from the second solution following the covalent coordination reaction. The organic-metal precursor material can be used for a source material in a CVD or ALD process by dissolving in a volatile solvent.

Figure 2:
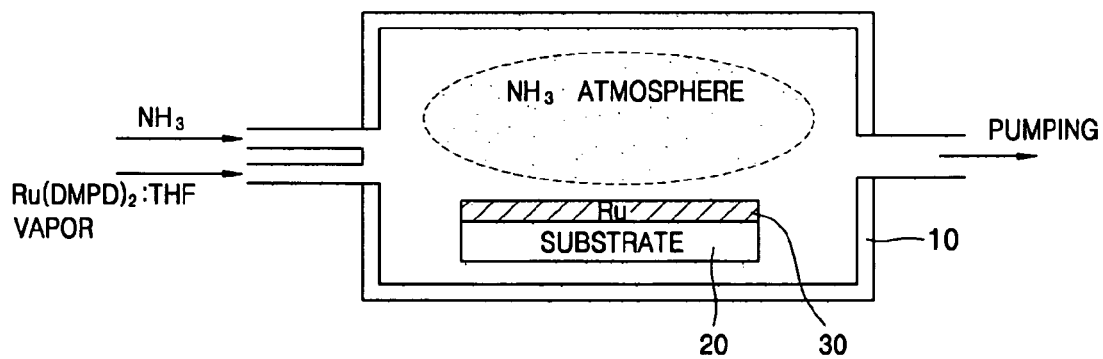
FIG. 2 is a schematic drawing of a chemical vapor deposition (CVD) process for manufacturing a metal thin film using an organic-metal precursor material according to an exemplary embodiment.

FIG. 2 is a schematic drawing of a chemical vapor deposition (CVD) process for manufacturing a metal thin film using an organic-metal precursor material according to an embodiment of the present invention.

After the organic-metal precursor material expressed by the chemical formula in FIG. 1 is prepared, a source gas is formed by evaporating the organic-metal precursor material at a temperature in the range of 150 to 250° C. A metal thin film 30 can then be deposited on a substrate 20 using CVD by supplying the source gas into a vacuum chamber 10 at a temperature of 250 to 500° C. Here, CVD also includes ALD.

Preferably, the metal thin film 30 is deposited under a reductive reaction gas atmosphere by further supplying a reductive reaction gas that includes $H_2$ or $NH_3$ into the vacuum chamber 10. The use of the reductive reaction gas can further weaken the bonding between the 2,4-dimethylpentadienyl ligand ("DMPD"), which is the primary ligand, and ruthenium (Ru), and accordingly, the organic-metal precursor material can be readily decomposed in the deposition process. Particularly, to activate the reductive reaction gas, plasma of the reductive reaction gas can be generated in the vacuum chamber 10, and the metal thin film 30 can be deposited under the reductive reaction gas plasma atmosphere. At this time, $H_2$ gas is supplied at a flow rate of 1 to 200 sccm, and $NH_3$ gas is supplied at a flow rate of 50 to 200 sccm. In an embodiment, the metal thin film comprises the reaction product of the organic-metal precursor material and a reducing reaction gas. In an embodiment, the reductive reaction gas atmosphere is free of oxygen.

The invention is further described in the following examples, which as are intended to be illustrative and should not be considered as limiting thereto.

EXAMPLE 1

Preparation of the Organic-metallic Precursor Compound

A first solution was obtained by dissolving 14.36 g (0.1 mol) of the ruthenium compound $Ru(DMPD)_2$ in 500 ml of dry, degassed pentane under inert atmosphere at room temperature. A second solution was obtained by adding 93.9 ml (0.6 mol) of dry, degassed THF to the first solution, and the second solution was stirred for 1 minute at room temperature to promote a covalent coordination reaction. The $Ru(DMPD)_2$-THF compound was obtained as a residue by vacuum distilling off the pentane from the second solution. A 0.2 M solution of the organic-metallic precursor compound $Ru(DMPD)_2$-THF was prepared using THF as a solvent, and this solution was used as a source material.

Figure 4:
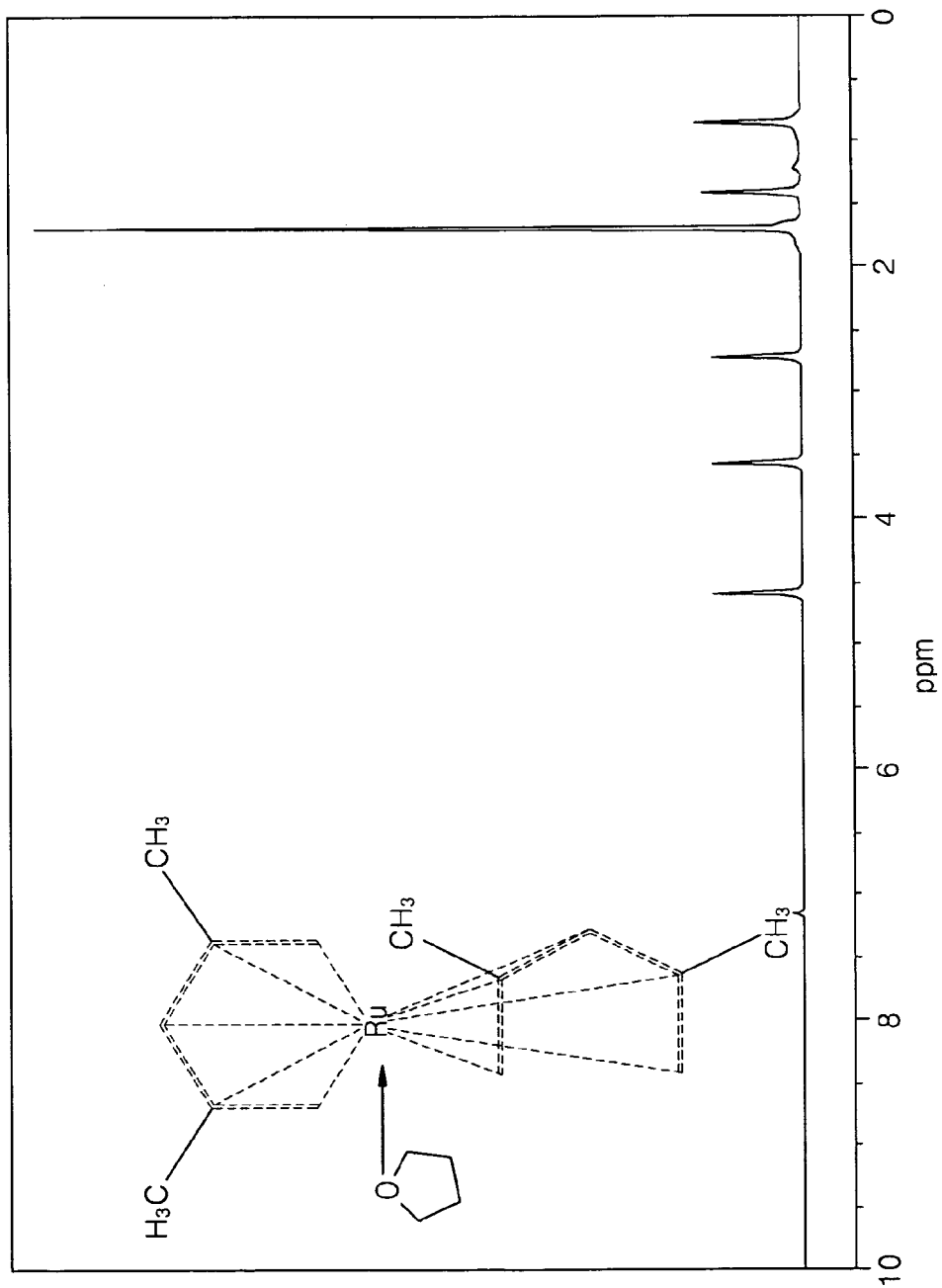
FIG. 4 is a graph showing the result of an NMR analysis of a ruthenium thin film manufactured using the CVD process of FIG. 2.

FIG. 4 is a proton nuclear magnetic resonance ($^1$H NMR) spectrum showing the proton resonances found in $Ru(DMPD)_2$-THF, as prepared according to Example 1.

EXAMPLE 2

Preparation of Metal Thin Films

The source material of Example 1 (0.2 M solution in pentane) was evaporated at a temperature of 150 to 250° C. and supplied to the vacuum chamber of a CVD tool. A ruthenium thin film of appx. 100 to 150 Å target thickness was deposited from the evaporated source material onto a $SiO_2$ or TiN substrate in the vacuum chamber, and the deposition was carried out under an oxygen-free $NH_3$ atmosphere by supplying $NH_3$ gas into the vacuum chamber at a flow rate of 50 to 200 sccm as a reductive reaction gas. Argon Ar gas was used as a conveying gas in the ruthenium thin film deposition process, and was supplied to the vacuum chamber at a flow rate of 50 to 1000 sccm.

Figure 3:
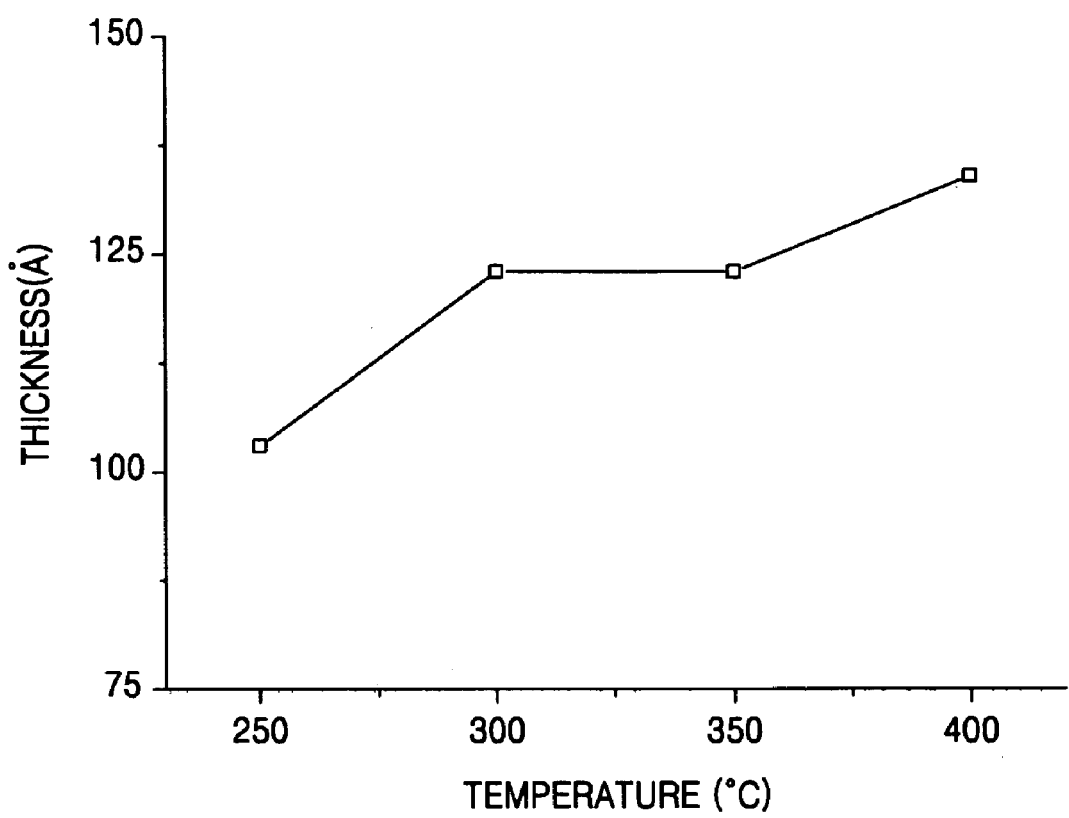
FIG. 3 is a graph showing the variation in thickness of a ruthenium thin film with deposition temperature in the CVD process of FIG. 2.

FIG. 3 is a graph showing the variation in thickness of a ruthenium thin film according to deposition temperature of the CVD process of FIG. 2. It can be seen in FIG. 3 that as temperature is increased, the thickness of the metal thin film increases as the deposition temperature is increased from 250 to 400° C., in approximately 50° C. increments.

Figure 5:
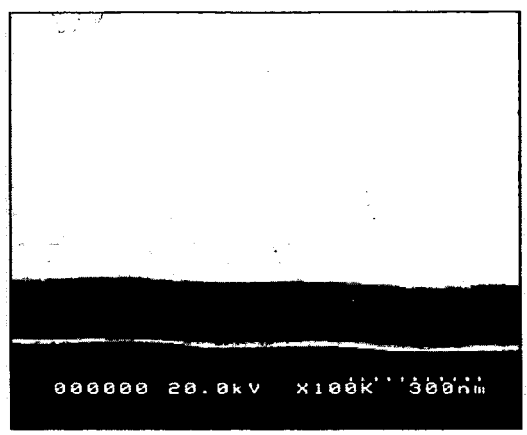
FIG. 5 is SEM images showing the change of a surface according to the annealing temperature of a ruthenium thin film manufactured using the CVD process of FIG. 2.
Figure 5:
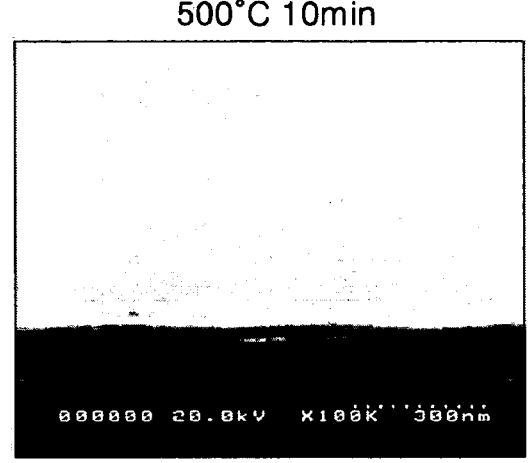
Figure 5:
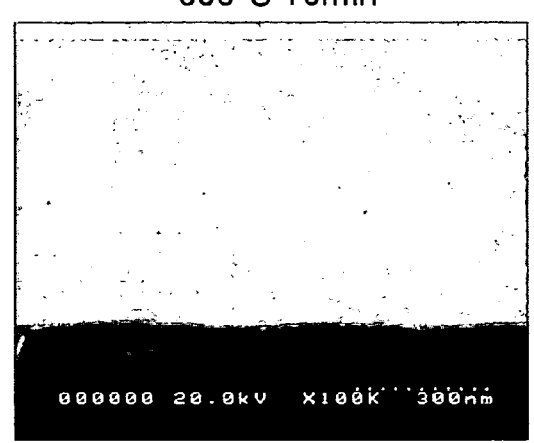

FIG. 5 shows scanning electron microscope ("SEM") images showing the change of surface morphology according to the annealing temperature of a ruthenium thin film manufactured using the CVD process of FIG. 2.

As disclosed herein, a new organic-metal precursor material that can be readily decomposed without reacting with an oxidant, and a method of manufacturing a metal thin film using the organic-metal precursor material, are both provided. The metal thin film can be deposited on a substrate using the organic-metal precursor material that is readily decomposable without reacting with an oxidant such as oxygen. Accordingly, the metal thin film manufactured in this way includes almost no oxygen, and may be thus considered free of oxygen. Therefore, when the organic-metal precursor material is used in the manufacture of an electrode material, or of a diffusion barrier film for blocking the diffusion of a wire material such as copper, eliminating oxygen from the metal thin film reduces or prevents the formation of oxides that can increase the specific resistances of the electrode material and/or the wire material. Also, the metal thin film manufactured according to the present invention has a surface morphology that is superior to the surface morphology of a conventional metal thin film that is prepared using a method that uses oxygen, and that therefore contains oxygen.

While the present invention has been shown and described with reference to exemplary embodiments thereof, it will be understood by those of ordinary skill in the art that various changes in form and detail may be made therein without departing from the spirit and scope of the present invention as defined by the following claims.

What is claimed is:

1. A method of manufacturing a metal thin film comprising:
preparing the organic-metal precursor material of the following chemical formula:

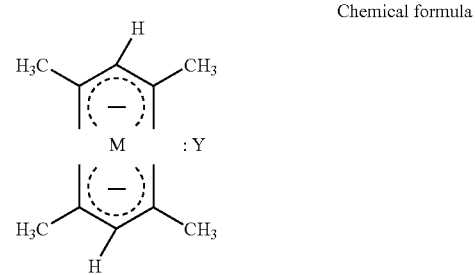

Chemical formula where M is Ru of Ir, and Y is an organic molecule having lone-pair electrons;
forming a source gas by evaporating the organic-metal precursor material; and
depositing a metal thin film on a substrate in a vacuum chamber using chemical vapor deposition (CVD) by supplying the source gas into the vacuum chamber.

2. The method of claim 1, wherein the organic-metal precursor material is evaporated at a temperature of 150 to 250° C.

3. The method of claim 1, wherein the metal thin film is deposited at a temperature of 250 to 500° C.

4. The method of claim 1, wherein the metal thin film is deposited under a reductive reaction gas atmosphere by further supplying a reductive reaction gas that comprises $H_2$ or $NH_3$ gas into the vacuum chamber.

5. The method of claim 4, wherein the $H_2$ gas is supplied at a flow rate of 1 to 200 sccm.

6. The method of claim 4, wherein the $NH_3$ gas is supplied at a flow rate of 50 to 200 sccm.

7. The method of claim 4, wherein the metal thin film is deposited under a reductive reaction gas plasma atmosphere by generating a reductive reaction gas plasma in the vacuum chamber.

8. The method of claim 4, wherein the reductive reaction gas atmosphere is free of oxygen.

9. The method of claim 1, wherein the CVD comprises atomic layer deposition (ALD).

10. The method of claim 1, wherein the organic molecule having lone-pair electrons is an organic molecule that comprises O, N, or P.

11. The method of claim 1, wherein the organic molecule having lone-pair electrons is a material selected from the group consisting of ether, amine, tetrahydrofuran (THF), a phosphine group, and a phosphite group.

12. The method of claim 1, wherein the preparing of the organic-metal precursor material comprises:

making a first solution by dissolving bis-2,4-dimethylpentanediyl ruthenium ($Ru(DMPD)_2$) or bis-2,4-dimethylpentanediyl iridium ($Ir(DMPD)_2$) in pentane;

making a second solution by adding an organic molecule having lone-pair electrons selected from the group consisting of an ether, an amine, tetrahydrofuran (THF), a phosphine, and a phosphite in the first solution;

stirring the second solution at room temperature to promote a covalent coordination reaction; and obtaining the organic-metal precursor material by vacuum distilling pentane from the second solution.

* * * * *